United States Patent [19]

Cue, Jr.

[11] 4,451,655

[45] May 29, 1984

[54] PROCESS FOR PREPARING CARBOLINE DERIVATIVES AND COMPOUNDS USED IN THEIR PREPARATION

[75] Inventor: Berkeley W. Cue, Jr., Groton, Conn.

[73] Assignee: Pfizer Inc., New York, N.Y.

[21] Appl. No.: 378,945

[22] Filed: May 17, 1982

[51] Int. Cl.$^3$ ............................................ C07D 471/04
[52] U.S. Cl. ...................................................... 546/85
[58] Field of Search ........................................... 546/85

[56] References Cited

U.S. PATENT DOCUMENTS 2,819,997  1/1956  McLamore ............................ 546/85
4,001,263  1/1974  Plattner et al. .................. 260/296 A

OTHER PUBLICATIONS

Dalton et al., Australian J. of Chem., (1969), vol. 22, pp. 185–195.
C. A. Harbert et al., in the *Journal of Medicinal Chemistry*, vol. 23, p. 635, (1980).

*Primary Examiner*—Henry R. Jiles
*Assistant Examiner*—Bernard Dentz
*Attorney, Agent, or Firm*—Charles J. Knuth; Peter C. Richardson

[57] ABSTRACT

A novel process for preparing various 2-substituted-5-aryl-1,2,3,4-tetrahydro-γ-carboline derivatives is provided, which involves (1) quaternizing a corresponding 5-aryl-γ-carboline compound with an appropriate aralkyl halide in the presence of sodium iodide, followed by (2) reduction of the corresponding quaternary carbolinium iodide salt intermediate with an alkali metal hydride to yield the desired final product. The latter compounds are known to be useful as tranquilizing agents, with 2-[4-(p-fluorophenyl)-4-hydroxybutyl]-5-(p-fluorophenyl)-8-fluoro-1,2,3,4-tetrahydro-γ-carboline representing a preferred final product. The aforesaid carbolinium salt intermediates as well as the corresponding 5-aryl-γ-carboline starting materials are all novel compounds.

14 Claims, No Drawings

PROCESS FOR PREPARING CARBOLINE DERIVATIVES AND COMPOUNDS USED IN THEIR PREPARATION

BACKGROUND OF THE INVENTION

This invention relates to a new and useful process for preparing various carboline derivatives which are of value in the field of chemotherapy. More particularly, it is concerned with a novel process for preparing certain 2-substituted-5-aryl-1,2,3,4-tetrahydro-γ-carboline derivatives, which are known to be useful as tranquilizing agents. The invention also includes the corresponding quaternary carbolinium iodide salt intermediates as well as the corresponding 5-aryl-γ-carboline starting materials, which are novel compounds.

In accordance with the prior art, a number of methods have been presented for preparing compounds of this particular type. For instance, in U.S. Pat. No. 4,001,263 to J. J. Plattner et al., there are described several different synthetic routes leading to the compounds of present interest, of which 2-[4-(p-fluorophenyl)-4-hydroxybutyl]-5-(p-fluorophenyl)-8-fluoro-1,2,3,4-tetrahydro-γ-carboline is an especially preferred embodiment. A typical route disclosed therein for preparing the preferred compounds of this particular class involves (1) treating the corresponding 2-unsubstituted-5-aryl-1,2,3,4-tetrahydro-γ-carboline starting material with an appropriate ω-haloalkyl phenyl ketone in order to effect alkylation at the 2-position of the molecule, followed by (2) reduction of the corresponding ketone intermediate with sodium borohydride to yield the desired final product having the requisite secondary alcohol side chain.

SUMMARY OF THE INVENTION

In accordance with the present invention, it has now been found possible to prepare various 2-substituted-5-aryl-1,2,3,4-tetrahydro-γ-carbolines by a novel two-step method starting from the corresponding 5-aryl-γ-carboline compound whereby the desired final products are readily obtained in pure form and in high yield. More particularly, the process of this invention involves preparing a compound of the formula:

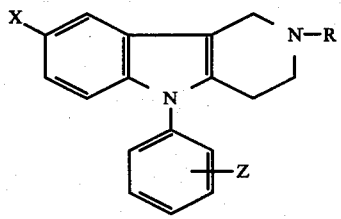

wherein X is hydrogen, fluorine, chlorine or bromine; Z is hydrogen, fluorine, chlorine or methoxy; and R is of the formula

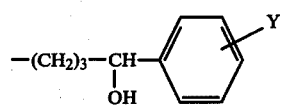

wherein Y is hydrogen, methyl, fluorine or chlorine, which comprises (a) contacting a corresponding 5-aryl-γ-carboline of the formula

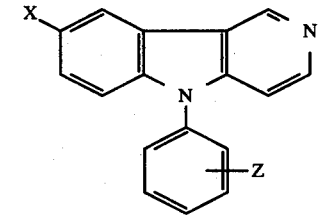

wherein X and Z are each as previously defined, in a reaction-inert polar organic aprotic solvent with at least an equimolar amount of an aralkyl halide of the formula

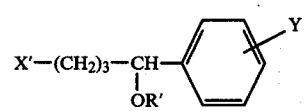

wherein X' is chlorine or bromine, Y is as aforesaid and R' is 2-tetrahydropyranyl, in the presence of a substantially equimolar amount of sodium iodide with respect to said aralkyl halide at a temperature ranging from at least about 60° C. up to the reflux temperature of the reaction mixture until the quaternization reaction to form the desired quaternary carbolinium iodide salt intermediate is substantially complete; and thereafter (b) subjecting the quaternary carbolinium salt formed in step (a) to the reducing action of an alkali metal hydride in a reaction-inert polar organic protic solvent at a temperature that is in the range of from about 10° C. up to about 35° C. until the reduction reaction to form the desired final product is substantially complete. In this way, a valuable therapeutic agent, such as 2-[4-(p-fluorophenyl)-4-hydroxybutyl]-5-(p-fluorophenyl)-8-fluoro-1,2,3,4-tetrahydro-γ-carboline (flutroline) is conveniently prepared in a most facile manner.

There is also included within the purview of this invention the novel quaternary carbolinium iodide salts produced in step (a) as intermediates useful for the production of the final products that have previously been described. The present invention therefore includes novel 2-substituted-5-aryl-γ-carbolinium iodide salts of the formula:

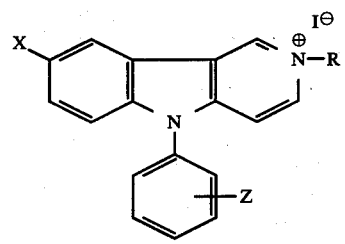

wherein X is hydrogen, fluorine, chlorine or bromine; Z is hydrogen, fluorine, chlorine or methoxy; and R is of the formula

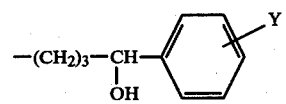

wherein Y is hydrogen, methyl, fluorine or chlorine. Preferred compounds in this category include those of the above formula wherein X, Y and Z are each fluorine and R is as previously described. A particularly preferred compound for these purposes is 2-[4-(p-fluorophenyl)-4-hydroxybutyl]-5-(p-fluorophenyl)-8-fluoro-γ-carbolinium iodide, as this is the intermediate that specifically leads to flutroline.

Additionally, the invention also includes within its purview the novel 5-aryl-γ-carboline starting materials used in step (a) to produce the aforesaid novel quaternary carbolinium iodide salt intermediates per se. Accordingly, the present invention also comprises novel compounds of the formula:

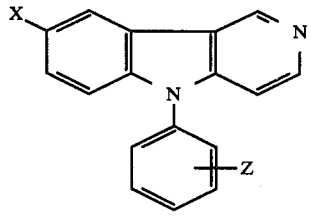

wherein X is hydrogen, fluorine, chlorine or bromine; and Z is hydrogen, fluorine, chlorine or methoxy. A particularly preferred compound for these purposes is 5-(p-fluorophenyl)-8-fluoro-γ-carboline, as this is the starting material that ultimately leads to flutroline.

DETAILED DESCRIPTION OF THE INVENTION

In accordance with the process of this invention, the molar ratio of the 5-aryl-γ-carboline starting material to the aralkyl halide reagent employed in step (a) is usually in the range of about 1.0:1.0 to about 1.0:2.0, respectively, in order to effect the desired quaternization reaction, which normally takes place within a period of about 24 to about 48 hours. The reaction is normally carried out in a reaction-inert polar organic aprotic solvent such as acetonitrile or a lower N,N-dialkyl alkanoamide having up to a total of five carbon atoms like dimethylformamide, diethylformamide and dimethylacetamide, etc. Upon completion of the reaction, the desired carbolinium iodide salt intermediate is readily recovered from the reaction mixture by first removing the solvent therefrom via evaporation under reduced pressure and then triturating the resultant residue with a suitable solvent such as diethyl ether, followed by washing in the usual manner and then further purification, if necessary, by means of recrystallization from an appropriate solvent system.

The quaternary carbolinium salt obtained in step (a) is then subjected to metal hydride reduction as described in step (b) and this is preferably accomplished by employing an alkali metal hydride such as sodium borohydride and the like for a period of time that is at least about one hour. The preferred solvent for the reaction is generally a lower alkanol having up to four carbon atoms such as methanol, ethanol or isopropanol, etc. Upon completion of the reduction step, water is added to the reaction mixture and the volatile liquids are thereafter removed by means of evaporation under reduced pressure. In this way, a crude product is ultimately obtained, which can easily be converted to a corresponding hydrohalide salt in a conventional manner, followed by subsequent conversion of the hydrohalide salt back to the desired final product (viz., the 2-substituted-5-aryl-1,2,3,4-tetrahydro-γ-carboline base) in substantially pure form.

The various 5-aryl-γ-carboline starting materials required for conducting the process of this invention are all novel compounds that are prepared in accordance with the convenient three-step procedure described in detail in Preparation A through Example 1. The required aralkyl halide reagents of choice are also novel compounds and their synthesis is respectively set forth in the procedure described in Preparations B-C.

As previously indicated, the 2-substituted-5-aryl-1,2,3,4-tetrahydro-γ-carboline final products afforded by the process of this invention are all valuable chemotherapeutic agents, useful mainly as tranquilizers, like 2-[4-(p-fluorophenyl)-4-hydroxybutyl]-5-(p-fluorophenyl)-8-fluoro-1,2,3,4-tetrahydro-γ-carboline (flutroline), for example. Hence, they are now provided in pure form and in high yield by the novel process of the present invention, which represents a major contribution to the economy in view of the greatly reduced nature of the costs involved.

PREPARATION A

A stirred solution consisting of 47.5 g (0.23 mole) of 4,4'-difluorophenylamine [M. M. Chen et al., Journal of Organic Chemistry, Vol. 26, p. 2721 (1961)] and 50.0 g. (0.26 mole) of 4-chloro-3-nitropyridine [S. Kruger et al., Journal of the Chemical Society (London), p. 2755 (1955)] dissolved in 70 ml. of tetramethylene sulfone was heated at 95° C. for a period of 24 hours. At the end of this time, an additional 6.5 g. (0.03 mole) of 4-chloro-3-nitropyridine was added to the mixture and heating at 95° C. was continued for a further period of 18 hours. Upon completion of this step, the temperature of the reaction mixture was allowed to cool to 60° C. and 300 ml. of water was added to the spent mixture. The resulting aqueous mixture was then layered with hexanes (400 ml.) and the two-phase system was thereafter stirred at 20° C. for a period of two hours to precipitate the desired product. The latter material was subsequently collected by means of suction filtration, washed well with water and then with hexanes and finally, recrystallized from isopropanol in the presence of activated carbon to afford 57.3 g. (76%) of pure 4-(4,4'-difluorodiphenylamino)-3-nitropyridine in the form of a yellow solid melting at 188.5°–189° C. The pure product was further characterized by means of mass spectroscopy and nuclear magnetic resonance data, in addition to elemental analysis.

Anal. Calcd. for $C_{17}H_{11}F_2N_3O_2$: C, 62.38; H, 3.39; N, 12.84. Found: C, 62.07; H, 3.45; N, 12.44.

PREPARATION B

To a stirred solution consisting of 61.0 g. (0.305 mole) of γ-chloro-p-fluorobutyrophenone (available from the Aldrich Chemical Company, Inc., Milwaukee, Wisconsin) dissolved in 400 ml. of ethanol, there were added 3.50 g. (0.09 mole) of sodium borohydride in a portionwise manner at 15° C. After stirring the resulting reaction mixture at this temperature for a period of one hour, the cooling bath was removed and the reaction was allowed to proceed at room temperature (~25° C.) for a period of approximately 16 hours (i.e., overnight). At this point, 4 ml. of concentrated hydrochloric acid was added cautiously to the reaction mixture at 0° C. After one hour, the solids were removed by means of suction filtration and the resulting filtrate was thereafter concentrated in vacuo to afford a pale yellow residual oil. The latter substance was then dissolved in diethyl ether, washed with aqueous sodium bicarbonate and dried over anhydrous sodium sulfate. Upon removal of the ether solvent by means of evaporation under reduced pressure, there were obtained 53.4 g. (88%) of pure 4-chloro-1-(p-fluorophenyl)-1-butanol as a pale yellow liquid. The pure product was characterized by means of nuclear magnetic resonance data.

PREPARATION C

A stirred solution consisting of 12.0 g. (0.06 mole) of 4-chloro-1-(p-fluorophenyl)-1-butanol (prepared as described in Preparation B) and 100 mg. (0.0004 mole) of p-toluenesulfonic acid dissolved in 500 ml. of dichloromethane was treated in a dropwise manner at 0° C. with a solution consisting of 27.7 g. (0.33 mole) of freshly distilled dihydropyran dissolved in 100 ml. of dichloromethane. After stirring the resulting reaction mixture at 0° C. for a period of two hours, the ice bath was removed and stirring was continued at room temperature (~25° C.) for a period of approximately 16 hours (i.e., overnight). The spent reaction mixture was then washed with saturated aqueous sodium bicarbonate solution, dried over anhydrous sodium sulfate and filtered to give a filtrate that was subsequently concentrated under reduced pressure. In this manner, there were ultimately obtained 11.6 g. (67%) of pure 1-[4-chloro-1-(p-fluorophenyl)butyl]-2-tetrahydropyranyl ether was a pale yellow liquid, b.p. 90°-96° C./0.8-1.0 mm. Hg. The pure product was further characterized by means of mass spectroscopy and nuclear magnetic resonance data.

EXAMPLE 1

In a 250 ml. Parr bottle under a nitrogen atmosphere, there were placed 250 mg. of 5% palladium-on-carbon catalyst (50% water-wet) and 5.0 g. (0.0153 mole) of 4-(4,4'-difluorodiphenylamino)-3-nitropyridine (prepared as described in Preparation A) dissolved in 50 ml. of glacial acetic acid. Under a hydrogen atmosphere (initial pressure, 50 p.s.i.g.), the reaction mixture was hydrogenated for a period of four hours. At this point, thin layer chromatography showed a complete conversion to the corresponding 3-amine, viz., 3-amino-4-(4,4'-difluorodiphenylamino)pyridine (m.p. 195°-198° C.). Consequently, the reaction mixture was filtered through a pad of supercel to remove the catalyst and the pad was subsequently washed with 50 ml. of glacial acetic acid.

The combined filtrates and washings were then cooled to 15° C. and 1.26 g. (0.0183 mole) of solid sodium nitrite was thereafter rapidly added thereto in one portion. The dark red solution which resulted was then gradually warmed to 110° C. over a two-hour period, during which time nitrogen gas was first observed to evolve at ca. 65° C. Upon completion of this step, i.e., when all gas evolution had ceased, heating was stopped and the solvent was subsequently evaporated in vacuo to afford a red oil as the residual material. The latter material was then layered with water and made strongly basic with aqueous sodium hydroxide solution so as to precipitate the crude product in the form of a brown solid. This solid was then dissolved in ethyl acetate and the resulting organic solution was subsequently treated with activated carbon and anhydrous magnesium sulfate. After removal of the solid matter by means of filtration and the solvent by means of evaporation under reduced pressure, there was finally obtained a solid product as residue. Recrystallization of the latter material from diethyl ether/hexanes then gave 3.58 g. (83%) of pure 5-(p-fluorophenyl)-8-fluoro-γ-carboline, m.p. 155°-159° C. The pure product was further characterized by means of mass spectroscopy and nulcear magnetic resonance data, in addition to elemental analysis.

Anal. Calcd. for $C_{17}H_{10}F_2N_2$: C, 72.85; H, 3.60; N, 10.00. Found: C, 72.83; H, 3.75; N, 10.02.

EXAMPLE 2

A solution consisting of 1.70 g. (0.00606 mole) of 5-(p-fluorophenyl)-8-fluoro-γ-carboline (prepared as described in Example 1), 1.50 g. (0.01 mole) of sodium iodide and 3.00 g. (0.0117 mole) of 1-[4-chloro-1-(p-fluorophenyl)butyl]-2-tetrahydropyranyl ether (prepared as described in Preparation C) dissolved in 50 ml. of acetonitrile was heated under reflux for a period of 48 hours. Upon completion of this step, the solvent was evaporated in vacuo to give an amber solid. Trituration of the latter material with diethyl ether then gave a pale yellow solid, which was subsequently washed with successive portions of diethyl ether, ethyl acetate and water. Recrystallization of the purified material from ethanol then gave 2.20 g. (63%) of pure 2-[4-(p-fluorophenyl)-4-hydroxybutyl]-5-(p-fluorophenyl)-8-fluoro-γ-carbolinium iodide, m.p. 270°-272° C. (decomp.). The pure product was further characterized by means of nuclear magnetic resonance data, as well as elemental analysis.

Anal. Calcd. for $C_{27}H_{22}F_3IN_2O$: C, 56.46; H, 3.86; N, 4.88. Found: C, 56.84; H, 3.71; N, 4.97.

EXAMPLE 3

To a stirred solution consisting of 575 mg. (0.001 mole) of 2-[4-(p-fluorophenyl)-4-hydroxybutyl]-5-(p-fluorophenyl)-8-fluoro-γ-carbolinium iodide (prepared as described in Example 2) dissolved in 20 ml. of methanol, there were added in a portion-wise manner 200 mg. (0.005 mole) of sodium borohydride at room temperature (~25° C.). After a period of one hour, 20 ml. of water was added and the volatile liquids were evaporated in vacuo. The crude product, which was now suspended in the aqueous mixture, was taken up in diethyl ether and the ether solution was subsequently dried over anhydrous magnesium sulfate. After removal of the drying agent by means of filtration, the resulting filtrate was thereafter chilled to 0° C. and treated with gaseous dry hydrogen chloride by bubbling same into the ether solution until no more product precipitated. The precipitated salt product was then collected by means of suction filtration and air dried to constant weight to ultimately afford 400 mg. (82%) of pure 2-[4-(p-fluorophenyl)-4-hydroxybutyl]-5-(p-fluorophenyl)-8-fluoro-1,2,3,4-tetrahydro-γ-carboline hydrochloride, m.p. 246°-248° C. (decomp.) [literature m.p. 246–248° C. (decomp.), according to C. A. Harbert et al., Journal of Medicinal Chemistry, Vol. 23, p. 635 (1980)].

The above hydrochloride salt was then converted to its free base by neutralization with aqueous sodium bicarbonate to give pure 2-[4-(p-fluorophenyl)-4-hydroxybutyl]-5-(p-fluorophenyl)-8-fluoro-1,2,3,4-tetrahydro-γ-carboline, m.p. 143.5°-145° C. A nuclear magnetic resonance spectrum of this material was found to be identical with that of an authentic sample of flutroline, prepared by the procedure described by C. A.

Harbert in the Journal of Medicinal Chemistry, Vol. 23, p. 635 (1980).

I claim:

1. A process for preparing a 2-substituted-5-aryl-1,2,3,4-tetrahydro-γ-carboline compound of the formula:

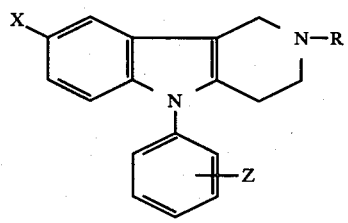

wherein
X is hydrogen, fluorine, chlorine or bromine;
Z is hydrogen, fluorine, chlorine or methoxy; and
R is of the formula

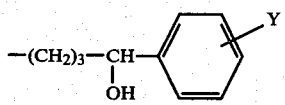

wherein Y is hydrogen, methyl, fluorine or chlorine, which comprises (a) contacting a corresponding 5-aryl-γ-carboline of the formula

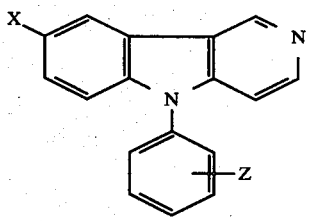

wherein X and Z are each as previously defined, in a reaction-inert polar organic aprotic solvent with at least an equimolar amount of an aralkyl halide of the formula

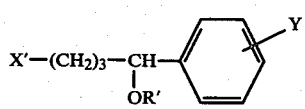

wherein X' is chlorine or bromine, Y is as aforesaid and R' is 2-tetrahydropyranyl, in the presence of a substantially equimolar amount of sodium iodide with respect to said aralkyl halide at a temperature ranging from at least about 60° C. up to the reflux temperature of the reaction mixture until the quaternization reaction to form the desired quaternary carbolinium iodide salt intermediate is substantially complete; and thereafter (b) subjecting the quaternary carbolinium salt formed in step (a) to the reducing action of an alkali metal hydride in a reaction-inert polar organic protic solvent at a temperature that is in the range of from about 10° C. up to about 35° C. until the reduction reaction to form the desired final product is substantially complete.

2. A process as claimed in claim 1 wherein the molar ratio of the 5-aryl-γ-carboline starting material to the aralkyl halide reagent is in the range of about 1.0:1.0 to about 1.0:2.0, respectively.

3. A process as claimed in claim 1 wherein the quaternization reaction is conducted for a period of about 24 to about 48 hours.

4. A process as claimed in claim 1 wherein the polar aprotic solvent employed in step (a) is selected from the group consisting of acetonitrile and a lower N,N-dialkyl alkanoamide having up to a total of five carbon atoms.

5. A process as claimed in claim 1 wherein said alkali metal hydride is sodium borohydride.

6. A process as claimed in claim 1 wherein the reduction reaction is conducted for a period of at least about one hour.

7. A process as claimed in claim 1 wherein the polar protic solvent employed in step (b) is a lower alkanol having up to four carbon atoms.

8. A process as claimed in claim 1 wherein X is fluorine, and Y and Z are each fluorine at the para-position of the aryl moiety.

9. A 2-substituted-5-aryl-γ-carbolinium iodide salt of the formula:

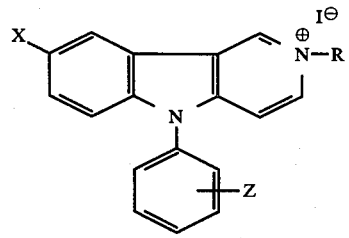

wherein
X is hydrogen, fluorine, chlorine or bromine;
Z is hydrogen, fluorine, chlorine or methoxy, and
R is of the formula:

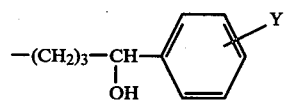

wherein Y is hydrogen, methyl, fluorine or chlorine.

10. A compound as claimed in claim 9 wherein X, Y and Z are each fluorine.

11. 2-[4-(p-Fluorophenyl)-4-hydroxybutyl]-5-(p-fluorophenyl)-8-fluoro-γ-carbolinium iodide.

12. A 5-aryl-γ-carboline compound of the formula:

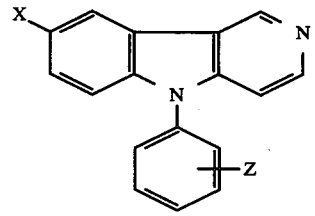

wherein X is hydrogen, fluorine, chlorine or bromine; and Z is hydrogen, fluorine, chlorine or methoxy.

13. A compound as claimed in claim 12 wherein X and Z are each fluorine.

14. 5-(p-Fluorophenyl)-8-fluoro-γ-carboline.

* * * * *